(12) United States Patent
Dickens et al.

(10) Patent No.: US 6,958,360 B2
(45) Date of Patent: Oct. 25, 2005

(54) ATTRACTANT PHEROMONE FOR THE COLORADO POTATO BEETLE

(75) Inventors: Joseph C. Dickens, Ellicott City, MD (US); James Oliver, Laurel, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 123 days.

(21) Appl. No.: 10/245,072

(22) Filed: Sep. 17, 2002

(65) Prior Publication Data

US 2003/0068352 A1 Apr. 10, 2003

Related U.S. Application Data

(60) Provisional application No. 60/325,395, filed on Sep. 27, 2001.

(51) Int. Cl.$^7$ .............................................. A01N 35/00
(52) U.S. Cl. .......................... 514/675; 424/84; 424/405
(58) Field of Search .................... 424/84, 405; 514/675

(56) References Cited

U.S. PATENT DOCUMENTS 5,849,317 A * 12/1998 Shorey ....................... 424/406

OTHER PUBLICATIONS

Webster—Dictionary Carrier p. 215, 1988.*
Hackh's —Dictionary, p. 136, 1969.*
Kyoonieus—Insect Suppression p. 262, 1982.*
Gill et al Pigments of Fungi Part 16– Synthesis—Tetrahedron: Asymmetry 1(7) 453–64, 1990.*
Devi et al MicroBiological Transformations of Terpenes—Indian J. Biochem. Biophys. 14(3) 288–291, 1977.*
Dickens, J.C., et al., "Breaking a Paradigm: Male–Produced Aggregation Pheromone for the Colorado Potato Beetle", *J. of Experimental Biology*, vol. 205, pp. 1925–1933, 2002.

Borden, J.H., et al., "Synthetic Juvenile Hormone: Induction of Sex Pheromone Production in *Ips confusus*", *Science*, vol. 166, pp. 1626–1627, Dec. 26, 1969.

Bandoni, A.L., et al., "Composition and Quality of the Essential Oil of Coriander (*Coriandrum sativum* L.) from Argentina", *J. Essent. Oil Res.*, vol. 10, pp. 581–584, Sep./Oct. 1998.

Edwards, M.A., et al., "Evidence for an Airborne Sex Pheromone in the Colorado Potato Beetle, *Leptinotarsa decemlineata*", *The Canadian Entomologist*, vol. 129, pp. 667–672, Jul./Aug. 1997.

Kurt Hansen, "Discrimination and Production of Disparlure Enantiomers by the Gypsy Moth and the Nun Moth" *Physiological Entomology*, vol. 9, pp. 9–18, 1984.

De Wilde, J., et al., "Responses to Air Flow and Airborne Plant Odour in the Colorado Beetle", *Neth. J. Pl. Path.*, vol. 75, pp. 53–57, 1969.

Arganosa, G.C., et al., "Seed Yields and Essential Oil of Northern–Grown Coriander (*Coriandrum sativum* L.)", *J. Herbs, Spices & Medicinal Plants*, vol. 6(2), pp. 23–32, 1998.

Louis Peyron, "Nouvelle methods de preparation de'esters d'acides aromatiques par esterification directs de l'acide par um alcool, en presence de dicyclohexylcarbodiimide," *Bull. Soc. Chim. Fr.*, No. 118, pp. 613–614, 1960.

(Continued)

*Primary Examiner*—Neil S. Levy
(74) *Attorney, Agent, or Firm*—John D. Fado; G. Byron Stover

(57) ABSTRACT

A method has been discovered for attracting Colorado potato beetles to an area of object or area, which method involves treating the object or area with a Colorado potato beetle attracting composition which contains a carrier material and a Colorado potato beetle attracting effective amount of (S)-3,7-dimethyl-2-oxo-oct-6-ene-1,3-diol.

19 Claims, 5 Drawing Sheets

OTHER PUBLICATIONS

H. Schmidt, et al., "Zur Kenntnis des vietnamesischen Citronellols", Arch. Pharm., vol. 296(8), pp. 554–548, 1963.

Sugawara, Y., et al., "Odor Distinctiveness between Enantiomers of Linalool: Difference in Perception and Responses Elicited by Sensory Test and Forehead Surface Potential Wave Measurement", Chem. Senses, vol. 25, pp. 77–84, 2000.

Cardé, R.T., et al., "Sexual Communication with Pheromones", In: Chemical Ecology of Insects, eds. W.J. Bell & R.T. Cardé, pp. 355–383, New York: Chapman & Hall.

Frighetto, N., et al., "Lippia alba Mill N.E. Br. (verbanaceae) as a Source of Linalool", J. Essent. Oil Res., vol. 10, pp. 578–580, Sep./Oct., 1998.

Gaydou, E.M., et al., "Application to the Determination of the Enantiomeric Purity of Linalool in Essential Oils", J. Chromatography, vol. 396, pp. 378–381, 1987.

Schantz, M.V., et al., "Abtrennung Von Terpenalkoholen Aus Terpengemischen Als 3,5–Dinitrobenzoate Auf Kieselgel–Dunnschichten", J. Chromatography, vol. 38, pp. 364–372, 1968.

Dubis, E., et al., "Sex–Dependent Composition of Cuticular Hydrocarbons of the Colorado Beetle, Leptinotarsa decemlineata Say", Comp. Biochem. Physiol., vol. 87A(4), pp. 839–843, 1987.

Mori, K., et al., Pheromone Synthesis, CXXXIII. Synthesis of Both the Enantiomers of (3Z,9Z)–cis–6, 7–Epoxy–3, 9–nonadecadiene, a Pheromone Component of Erranis defoliaria, Synthesis, pp. 1125–1129, Dec., 1991.

Palaniswamy, P., et al., "Modulation of Sex Pheromone Perception in Female Moths of the Eastern Spruce Budworm, Choristoneura fumiferana by Altosid", J. Insect. Physiol., vol. 25, pp. 571–574, 1979.

Levison, H.Z., et al., "Sex Recognition by a Pheromone in the Colorado Beetle", Naturwissenschaften, vol. 66, pp. 472–473, 1979.

Schütz, S., et al., "Host Plant Selection of the Colorado Potato Beetle as Influenced by Damage Induced Volatiles of the Potato Plant", Naturwissenschaften, vol. 84, pp. 212–217, 1997.

Murray, K.D., et al., "Citrus Limonoid Effects on the Colorado Potato Beetle Larval Survival and Development", Entomologia Experimentalis et Applicata, vol. 80, pp. 503–510, 1996.

Gilles Boiteau, "Sperm Utilization and Post–Copulatory Female–Guarding in the Colorado Potato Beetle, Leptinotarsa decemlineata", Entomol. exp. appl., vol. 47, pp. 183–187, 1988.

J.H. Visser, "The Design of a Low–Speed Wind Tunnel as an Instrument for the Study of Olfactory Orientation in the Colorado Beetle", Ent. exp. & appl., vol. 20, pp. 275–288, 1976.

Heath, R.R., et al., "An Automated System for use in Collecting Volatile Chemicals Released fr m Plants", J. Chemical Ecology, vol. 20(3), pp. 593–608, 1994.

Landolt, P.J., et al., "Effects of Host Plant, Gossypium hirsutum L., On Sexual Attraction of Cabbage Looper Moths Trichoplusia ni (Hübner) (Lepidoptera: noctuidae)", J. Chemical Ecology, vol. 20(11), pp. 2959–2974, 1994.

Peng, C., et al., "Male Crucifer Flea Beetles Produce an Aggregation Pheromone", Physiological Entomology, vol. 24, pp. 98–99, 1999.

Jermy, T., et al., "Method for Screening Female Sex Pheromone Extracts of the Colorado Potato Beetle", Entomol. exp. appl., vol. 59, pp. 75–78, 1991.

Hans Visser, J., et al., "An Open Y–Track Olfactometer for Recording of Aphid Behavioural Responses to Plant Odours", Proceedings of the Section Experimental & Applied Entomology of the Netherlands Entomological Society Amsterdam, vol. 9, pp. 41–46, 1998.

Dickens, J.C., et al., "Effects of Antennectomy and a Juvenile Hormone Analog on Pheromone Production in the Boll Weevil (Coleoptera: curculionidae)", J. Entomol. Science, vol. 23(1), pp. 52–58, Jan., 1988.

Dickens, J.C., et al., "Enhancement of Insect Pheromone Responses by Green Leaf Volatiles", Naturwissenschaften, vol. 77, pp. 29–31, 1990.

J.C. Dickens, "Specificity in Perception of Pheromones and Host Odours in Coleoptera", In Mechanisms in Insect Olfaction (eds. T. L. Payne, M. C. Birch and C. Kennedy), pp. 253–261, Oxford, U. K., Oxford University Press).

J.C. Dickens, "Green Leaf Volatiles Enhance Aggregation Pheromone of Boll Weevil, Anthonomus grandis", Entomol. exp. appl., vol. 52, pp. 191–203, 1989.

Renwick, J.A.A., et al., "Control of Pheromone Production in the Bark Beetle, Ips cembrae", Physiological Entomology, vol. 4, pp. 377–381, 1979.

N.E. McIndoo, "An Insect Olfactometer", J. Econ. Entomol., vol. 19, pp. 545–571, 1926.

Rama, J., et al., "Microbiological Transformations of Terpenes: Part XXIV–Pathways of Degradation of Linalool, Geraniol, Nerol & Limonene by Pseudomonas incognita (Linalool Strain)", Indian Journal of Biochemistry & Biophysics, vol. 14, pp. 359–363, Dec., 1977.

Otto, D., "Further Evidence for the Presence of a Female Sex Pheromone in the Colorado Potato Beetle Leptinotarsa decemlineata Say. and its Biological Characterization", In Practice Oriented Results on the Use and Production of Neem Ingredients and Pheromones IV (eds. H. Kleeberg and V. Micheletti), pp. 135–147, Lahnau, Germany: Trifolio–M GmbH), 1996.

J.C. Dickens, "Predator–Prey Interactions: Olfactory Adaptations of Generalist and Specialist Predators", Agricultural and Forest Entomology, vol. 1, pp. 47–54, 1999.

Bolter, C.J., et al., "Attraction of Colorado Potato Beetle to Herbivore–Damaged Plants During Herbivory and After its Termination", J. Chemical Ecology, vol. 23(4), pp. 1003–1023, 1997.

J. Devi et al., Abstract, "Microbiological transformations of terpenes. Part XXIII. Fermentation of geraniol, nerol and limonene by a soil pseudomonad, Pseudomonas incognita (Linalool strain)", Indian J. Biochem. Biophys.,vol. 14(3), pp. 288–291, 1977.

M. Gill et al., Abstract, "Pigments of gungi. Part 16. Synthesis of methyl (R)–(+)–tetrahydro–2–methyl–5–oxo–2–furanacetate and its (S)–(–) antipode, chiroptical refer- ences for determination of the absolute stereochemistry of fungal preanthraquinones", Tetrahedron: Asymmetry, vol. 1(7), pp. 453–464, 1990.

* cited by examiner

A. Undamaged plant

C. Females feeding on plant

B. Mechanically-damaged plant

D. Males feeding on plant

A. Single cell
1. Control
2. Racemate
3. (S)-enantiomer
4. (R)-enantiomer

Source load 100ng

B. Electroantennogram

GC injection 10ng

Bar represents 500 msec stimulation.

ATTRACTANT PHEROMONE FOR THE COLORADO POTATO BEETLE

REFERENCE TO RELATED APPLICATION

This application claims the benefit of U.S. Provisional Application No. 60/325,395, filed Sep. 27, 2001, which is incorporated herein by reference in its entirety.

BACKGROUND OF THE INVENTION

The present invention relates to an attractant composition for Colorado potato beetles, which composition contains a carrier material and a Colorado potato beetle attracting effective amount of (S)-3,7-dimethyl-2-oxo-oct-6-ene-1,3-diol. The present invention also relates to a method for attracting Colorado potato beetles to an object or area, which method involves treating the object or area with a Colorado potato beetle attracting composition which contains a carrier material and a Colorado potato beetle attracting effective amount of (S)-3,7-dimethyl-2-oxo-oct-6-ene-1,3-diol.

Insect behavior is governed by complex interactions among chemical and physical signals in the environment. For example, host plant volatiles may (1) facilitate orientation of insects to potential feeding sources (Bernays, E. A., and R. F. Chapman, 1994, Host Plant Selection by Phytophagous Insects, xiii+312p, New York, N.Y., Chapman & Hall); (2) provide a mechanism for insects to avoid nonhosts (Dickens, J. C., et al., Experientia, 48: 523–524 (1992)); or (3) either enhance behavioral responses to pheromones (Dickens, J. C., Ent. exp. Appl., 52: 191–203 (1989); Dickens, J. C., et al., Naturwissenschaften, 77: 29–31 (1990)) or disrupt behavioral responses to pheromones (Dickens, J. C., et al., Experientia, 48: 523–524 (1992)). Insect-produced volatiles or pheromones attract conspecifics for mating (Cardé, R. T., and T. C. Baker, 1984, Sexual communication with pheromones, In Chemical Ecology of Insects (eds. W. J. Bell and R. T. Cardé), pp. 355–383, New York: Chapman & Hall) or disrupt behavioral responses of closely related species (Hansen, K., Physiol. Entomol., 9: 9–18 (1984); Borden, J. H., 1997, Disruption of semiochemical-mediated aggregation in bark beetles, In Insect Pheromone Research New Directions (eds. Cardé, R. T. and Minks, A. K.), pp. 421–438, New York, N.Y.: Chapman & Hall).

The existence of a sex attractant pheromone for the Colorado potato beetle (CPB) *Leptinotarsa decemlineata* (Say) (*Coleoptera:Chrysomelidae*) has been a subject of dispute. Boiteau (Boiteau, G., Ent. exp. Appl., 47: 183–187 (1988)) considered that plant odors attracted both sexes to the crop where sexual encounters were at random. The existence of a short-range or contact sex pheromone on the elytra of female CPB that elicited copulatory behavior in males was first shown by Levinson et al. (Levinson, H. Z., et al., Naturwissenschaften, 66: 472–473 (1979)) and later verified by others (Jermy, T., et al., Ent. Exp. Appl,. 59: 75–78 (1991); Otto, D., 1996, Further evidence for the presence of a female sex pheromone in the Colorado potato beetle *Leptinotarsa decemlineata* Say. and its biological characterization, In Practice Oriented Results on Use and Production of Neem Ingredients and Pheromones IV (eds. H. Kleeberg and V. Micheletti), pp. 135–147, Lahnau, Germany: Trifolio-M GmbH).

Prior to the work of Boiteau (1988) cited above, DeWilde et al. (DeWilde, J.; et al., Netherlands J. Plant Pathol., 75: 53–57 (1969)) observed that female emissions enhanced the anemotactic response of males in a laboratory behavioral bioassay. Experiments by Levinson at al. (Levinson, H. Z., et al, Naturwissenschaften, 66: 472–473 (1979)) showed that males responded differentially to male and female extracts from a distance of 8 mm. These observations could not be verified in a different behavioral assay in which male CPB did not show any sign of percepting the presence of females kept in small cages. Later Edwards and Seabrook (Edwards, M. A., and W. D. Seabrook, Canad. Entomol., 129: 667–672 (1997)) demonstrated that males move upwind towards females from a distance of at least 50 cm. Their results were based on greenhouse studies where all possible sex combinations placed on potted potato plants were tested; however, only 22% (11 of 49) of male beetles moved toward the female containing plant.

Based on laboratory behavioral studies in which antennal segments were selectively extirpated, olfactory receptors for the sex attractant pheromone in male CPB were thought to be located on the terminal and penultimate antennal segments (DeWilde, J., et al., Netherlands J. Plant Pathol., 75: 53–57 (1969)). Electroantennograms elicited by pentane extracts of female beetles were nearly twice as large as those elicited by extracts of males or potato foliage (Levinson, H. Z., et al, Naturwissenschaften, 66: 472–473 (1979)). Dubis et al. (Dubis, E. E., et al., Comp. Biochem. Physiol., 87A: 839–843 (1987)) demonstrated chemical differences in cuticular hydrocarbons of male and female beetles; such differences could function in the recognition of females by males and as a releaser of copulatory behavior.

We report herein the discovery of a male-specific compound ((S)-3,7-dimethyl-2-oxo-oct-6-ene-1,3-diol (CPB I)) released by males feeding on potato plants; this compound is absent in collections of volatiles from females feeding on potato plant. Both male and female CPB are attracted to CPB I in laboratory behavioral bioassays. Since the accepted paradigm for chrysomelid beetles in general (Mayer, M. S., and J. R. McLaughlin (1991), Handbook of Insect Pheromones and Sex Attractants, Boca Raton, Fla.: CRC Press, 1083 pp.), and the CPB in particular (DeWilde, J., et al., Netherlands J. Plant Pathol., 75: 53–57 (1969); Edwards, M. A., and W. D. Seabrook, Canad. Entomol., 129: 667–672. (1997), was a female-produced attractant pheromone, our discovery of a male-produced pheromone in CPB surprisingly breaks the previous paradigm and provides a new model for chemical communication in these insects.

SUMMARY OF THE INVENTION

In accordance with the present invention there is provided an attractant composition for Colorado potato beetles, which composition contains a carrier material and a Colorado potato beetle attracting effective amount of (S)-3,7-dimethyl-2-oxo-oct-6-ene-1,3-diol.

Also in accordance with the present invention is a method for attracting Colorado potato beetles to an area of object or area, which method involves treating the object or area with a Colorado potato beetle attracting composition which contains a carrier material and a Colorado potato beetle attracting effective amount of (S)-3,7-dimethyl-2-oxo-oct-6-ene-1,3-diol.

DETAILED DESCRIPTION OF THE INVENTION

Figure 1:
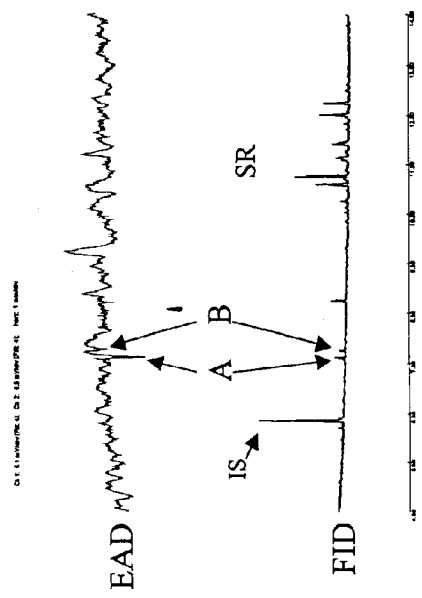
FIG. 1 shows gas chromatography (FID) with coupled electroantennograms (EAD) from Colorado potato beetle (CPB) in response to volatiles emitted over a 3 hour test period by undamaged potato plant (A), mechanically-damaged potato plant (B), ten female CPB feeding on a potato plant (C), and ten male CPB feeding on a potato plant. A=nonanal; B=2-phenyl ethanol; CPB I=male-specific compound; IS=internal standard (10 ng of decane); Sesquiterpene region=retention times of various sesquiterpenes.
Figure 1:
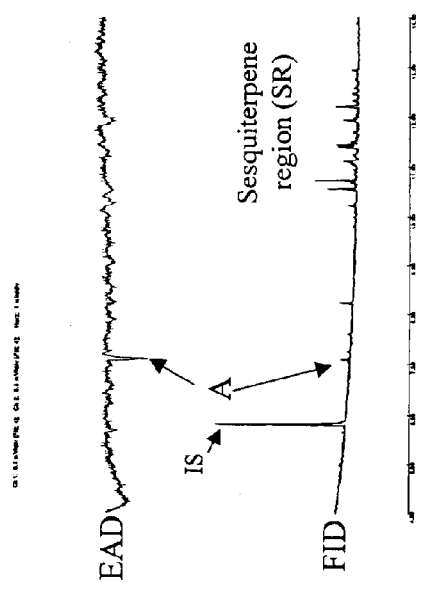
Figure 1:
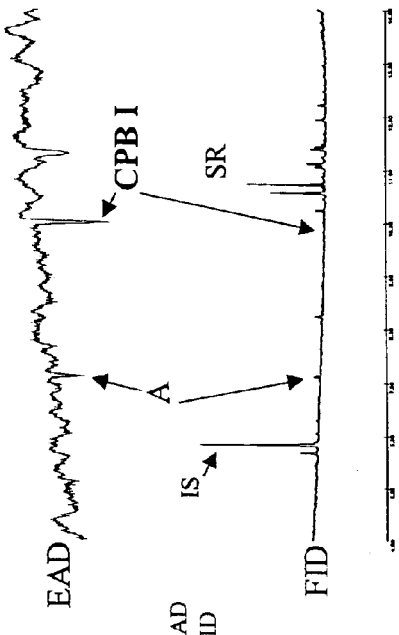
Figure 1:
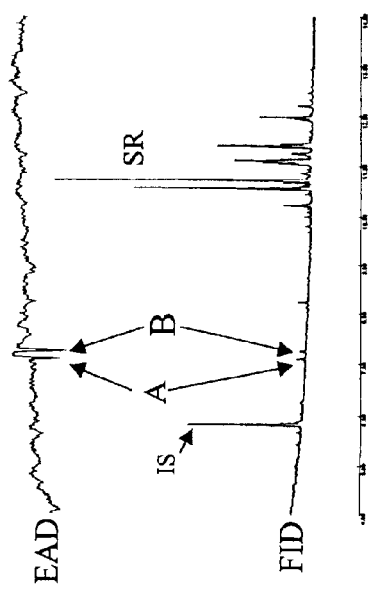

A method is disclosed for attracting Colorado potato beetles to an object or area, comprising treating the object or area with a Colorado potato beetle attracting composition comprising a carrier material and a Colorado potato beetle attracting effective amount of (S)-3,7-dimethyl-2-oxo-oct-6-ene-1,3-diol.

The attractant of the present invention is applied with a carrier component. The carrier component can be a liquid or a solid material. As is known in the art, the vehicle or carrier to be used refers to a substrate such as a membrane, hollow fiber, microcapsule, cigarette filter, gel, polymers, or the like. All of these substrates have been used to release insect attractants in general and are well known in the art.

The amount of attractant used will be at least an effective amount. The term "effective amount," as used herein, means the minimum amount of attractant needed to attract the Colorado potato beetle to a treated area or object when compared to the same area or object which is untreated. Effective concentrations of the attractant in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would attract more than 50% of the beetles and would be statistically significant in comparison to a control. The attractant composition may or may not contain a control agent for Colorado potato beetles, such as a biological control agent or an insecticide known in the art to kill Colorado potato beetles. Other compounds may be added to the attractant composition provided they do not substantially interfere with the intended activity of the attractant composition; whether or not a compound interferes with attractant activity can be determined, for example, by the procedure utilized below. Such other compounds could include natural or synthetic blends of volatiles emitted by potato plants (e.g., (a) (Z)-3-hexenyl acetate, (±)-linalool, nonanal, and methyl salicylate; (b) (Z)-3-hexenyl acetate, (±)-linalool, and methyl salicylate; (c) (Z)-3-hexen-1-ol, (E)-2-hexen-1-ol, and (±)-linalool; (d) (Z)-3-hexenyl acetate and methyl salicylate; (e) (Z)-3-hexenyl acetate and (±)-linalool (Dickens, J. C., Agric. Forest Entomol., 2: 167–172 (2000)); (f) (Z)-3-hexen-1-ol, (E)-2-hexen-1-ol, (±)-linalool, nonanal, and methyl salicylate; (g) nonanal; (h) 2-phenylethanol; (i) 2-phenylethanol and (±)-linalool; or (j) 2-phenylethanol and nonanal); such other compounds could include at least one member selected from the group consisting of (Z)-3-hexenyl acetate, (+)-linalool, nonanal, methyl salicylate, (Z)-3-hexen-1-ol, (E)-2-hexen-1-ol, nonanal, 2-phenylethanol, and mixtures thereof. Such other compounds may be present from about 0.0025% to about 20% in the composition.

The attractants could be used in pest management strategies: (1) as a component of an attracticide which combines it with a feeding stimulant and lethal doses of insecticide or pathogen. Such an attracticide would not only specifically target CPB populations but would also result in an overall decrease in application rates for pesticides to potato crop ecosystems; (2) for monitoring populations of colonizing adult beetles early in the season; (3) in deployment of the trap crop method of CPB control; (4) to indicate CPB movement within potato fields; or (5) in conjunction with antifeedants (Murray, K. D., et al., Entomol. Exp. Appl., 80: 503–510 (1996)) in "push-pull" strategies of insect management.

The following examples are intended only to further illustrate the invention and are not intended to limit the scope of the invention as defined by the claims.

EXAMPLES

Materials and Methods:

Insects: Adult Colorado potato beetle (CPB), *Leptinotarsa decemlineata* Say, were obtained from a colony infused every year with field collected insects, all life stages were reared on *Solanum tuberosum* var. *Kennebeck*. Emerging adults were collected daily, identified to gender, and isolated in petri dishes with moistened filter paper and fresh potato foliage that was replenished daily. Insects were kept in an environmental chamber (16L:8D) at 25° C. until use. For volatile collections, insects greater than 11 days old were used.

Collection of Plant and Insect Volatiles:

Potato plants, *Solanum tuberosum* var. *Kennebeck*, were grown in a greenhouse under 16L:8D at 25° C. in potting soil/vermiculite mix (Jiffy mix). Undisturbed, single stem potato plants were used for volatile collections. Plants were approximately 35 cm in height and 5–7 weeks old.

An automated volatile collection system (Analytical Research Systems, Inc., Gainesville, Fla.) modified from one described by Heath and Manukian (Heath, R. R., and A. Manukian, J. Chem. Ecol., 20: 593–608 (1994)) was used for collection of plant and insect produced volatile chemistry. The system consists of a humidified air delivery system (HADS) with mass flow controllers to regulate airflow into a volatile collection chamber (VCC). An inlet took laboratory air, regulated to 60 psi (420 KPa), which was then filtered and further regulated to 18.5 psi (125 KPa). The air was split to dry and wet air lines, controlled to 1–3 liters/minute flow rate, and either passed directly or bubbled through distilled and deionized water and into the VCC. Two glass VCCs were used: a 45 L carboy for collection of volatiles from individual plants or insects feeding on a plant, and a 3 L jar for collection of volatiles from insects alone. The 45 L carboy sat atop a guillotine base assembly with two teflon-coated blades coming together in a tongue-and-groove joint, a 2.5 cm diameter hole lined with cotton enclosed and sealed around the plant stem. A manifold lid with eight ports to hold volatile collection traps (VCT) was attached to the top of the chambers with an O-ring and C-clamp. VCTs were of glass tubes 8 cm in length, 0.5 cm outside diameter (0.4 mm id), and filled with 30 mg of 80/100 mesh Super-Q as the adsorbent. Air was pulled through individual VCTs with an Automated Volatile Collection System (AVCS) consisting of a vacuum (−80 KPa) regulated to −34 KPa and controlled to 1–2 litres/minute with a mass flow controller. Solenoid switches, controlled with a GE Fanuc PLC programmed with Timed Event Sequencing Software (ARS, Inc., Gainesville, Fla.), controlled air sampling through eight valves attached to VCTs with tygon tubing.

Following collection of volatiles, chemicals were extracted from VCTs with 100 ml hexane; 50 $\mu$l was collected in 300 $\mu$l cone vials for GC/EAD analysis. Ten ng/$\mu$l of n-decane was added to each sample as an internal standard. After each collection, the VCCs were washed with warm soap and water, rinsed with distilled water, then rinsed two times each with acetone followed by hexane. Following extraction of VCTs, each trap was rinsed four times with 200 $\mu$l hexane. Prior to each collection, one VCT was rinsed with 100 $\mu$l hexane, which was collected and injected onto a GC to check for contamination.

Volatiles were collected from undamaged or mechanically damaged potato plants, and plants being fed upon by CPB males or females. Plants were placed into the 45 L carboy and volatile collections were made continuously for a 24 hour period; eight VCTs were collected for three hours per trap. A light shield consisted of a wood frame 52×52×70 cm draped with a double layer of black felt. The shield covered the 45 L VCC to simulate lighting conditions in the greenhouse (16:8 l:d). Undamaged plants were placed undisturbed into the VCC. Mechanically damaged plants were placed into the chamber after cutting five 1 cm long incisions around the perimeter of six leaves with dissection scissors washed in methanol. Volatiles from plants infested with 10 males or 10 females were also collected.

Volatiles were collected from male CPB feeding on 4.8 g of potato foliage in the 3 L VCC. Collections were made continuously for a 24-hour period with a single VCT. Subsequently, volatiles from groups of 20 female CPB were similarly collected in the 3 L VCC continuously for 24 hours with a single VCT.

GC/EAD analysis of volatile collections: One microlitre samples of volatile collections were injected into a Hewlett Packard™ Model 5890A gas chromatograph (GC) equipped with an HP-5 capillary column (crosslinked 5% PH ME Siloxane; film thickness 0.25 $\mu$m; length 30 m; i.d. 0.25 mm) and flame ionization detector (FID). The effluent from the column was split using a Gerstel™ GraphPack-3D/2 splitter with a ratio of ~1 to the GC (FID): 4 to an electroantennogram preparation of a CPB adult (EAD). The EAD preparation was an adult CPB antenna removed and mounted between two glass capillary electrodes filled with 0.1M NaCl. Ag—AgCl wires in the glass capillaries. An effluent conditioning assembly to carry GC effluent over a CPB antennal preparation, hardware, and software for data collection and analyses using a computer were obtained from SYNTECH (Hilversum, the Netherlands). After an initial temperature of 50° C. held for 2 minutes following injection, the GC oven increased at 15° C./min to 235° C. which was held for 8 minutes.

Isolation and Identification of Male Specific Compound:

In an attempt to increase production of the male specific compound, males were subject to the following treatments: JHIII in acetone, extirpation of both antennae, and extirpation of both antennae+JHIII in acetone. All treatments were repeated at least three times. For the JHIII treatment, 2 ml of a 5 $\mu$g/ml solution of JHIII was applied to the prothoracic sternum between the coxae. Antennae were removed at the third segment from the proximal end. All treatments were performed 1 hour before placing beetles into the VCC. For the treatment with both antennae removed+JHIII, three separate collections were made continuously for at least seven days following treatment. The collection chamber was cleaned, rinsed, and fresh foliage added daily.

The major GC/EAD active component in volatiles collected by aeration of feeding CPB males was isolated in pure form for nuclear magnetic resonance (NMR) spectroscopy by using a Gerstel (Baltimore, Md.) automated preparative fraction collector (PFC) connected to a HP 6890 gas chromatograph with hydrogen as carrier gas at 50 cm/sec. Six Gerstel 100 $\mu$L U-shaped glass traps that had been baked overnight at 220° C. were plumbed into the PFC and were cooled to 0° C. in an ethanol bath. The PFC switching valve and transfer line were held constant at 200° C. The HP 6890 injector, fitted with a Tenax-packed insert, was operated in the solvent venting mode; 59° C. at manual injection with hexane as solvent, solvent venting 100 ml/min for 0.45 min followed by heating to 250° C. at 600° C./min. The chromatographic column (HP-1, 60 m×0.53 ID, 5 $\mu$m film thickness) was held at 46° C. for 1.6 min after injection and then heated to 220° C. at 30° C./min. Column effluent was split ca. 95 parts to the PFC and 5 parts to a flame ionization detector. These operating conditions were developed using 2-dodecanone as standard because it had chromatographic retention indices like the active CPB compound, and they afforded ca. 70–80% recovery of the chromatographed standard. Five sequential 3–4 $\mu$L injections of combined and concentrated hexane aeration extracts with collection in one trap over 16–17.25 min of each chromatographic run yielded ca. 1 mg pure compound. Ends of the trap were sealed with small rubber septa, and the compound was subsequently eluted into an nmr tube with deutero-solvent for analysis and structure determination for the biologically active CPB compound.

NMR spectra were obtained with a JEOL Model Eclipse+ 500 with deuterobenzene as solvent. Proton spectra were recorded at 500 MHz and $^{13}$C-spectra at 125 MHz. Mass spectra were recorded with a Shimadzu GCMS-QP5050A spectrometer or with a Hewlett Packard Model 5973 mass selective detector. Electron ionization spectra were collected at 70 eV, and ammonia and deuteroammonia were employed as reagent gases for chemical ionization spectra. Optical rotations were measured on chloroform solutions using a Perkin-Elmer Model 241 automatic polarimeter operated at the sodium-D (589 nm) wavelength. Mention of a proprietary product or company does not imply endorsement.

Assays of Biological Activity of Male Specific Compound:

Sensitivity of antennal olfactory receptors for the racemate and optical isomers of the male specific compound were tested using coupled GC/EAD and single sensillum recording techniques. GC/EAD tests involved injection of 1 μl of serial dilutions of 3,7-dimethyl-2-oxo-oct-6-ene-1,3-diol (CPB I).

Chemical blends and plant foliage were tested for behavioral activity in an open Y-track olfactometer modified after Visser and Piron (Visser, J. H., and P. G. M. Piron, Proceedings of the Section Experimental and Applied Entomology of the Netherlands Entomological Society Amsterdam, 9: 41–46 (1998)) and described in detail by Dickens (Dickens, J. C., Agric. Forest Entomol., 1: 47–54 (1999)). In brief, odorous stimuli emanating from volatile collections from CPB males feeding on potato plants or the male-specific compound on filter paper discs (2.5 cm dia.; Whatman™ #1 filter paper) in Ehrlenmeyer flasks were delivered to either side of the device. Hydrocarbon free air that was humidified by passing through distilled water carried the odor molecules to either arm of the bioassay apparatus. Treatments were replenished after 30 min of use in the bioassay apparatus. Airflow was regulated to 1 l/min by flowmeters. Experiments were conducted in a darkened room at 22° C. in which the only source of light was that associated with the bioassay device. For all bioassays, at least 20 males and 20 females were tested.

Volatile collections from male CPB feeding for three hours on a potato plant and serial dilutions of the male specific compound were tested as 10 μl aliquots placed on a filter paper disc as described above. The male specific compound was tested at 1.0 μg/10 μl solvent (hexane) and in a dilution series ranging from 0.0001 to 1.0 μg/10 μl solvent.

Prior to testing at age 7–14 days, unmated insects were held individually in 5.5 oz. cups, provided with fresh potato foliage on a continuous basis, and maintained under incubator conditions of a 16:8 light:dark cycle, 80–90% R.H., and "day" and "night" temperatures of 25° C. and 23° C., respectively. On the day of testing, insects were transferred to smaller 1 oz. cups and held for 1–3 hrs with moist filter paper but no foliage, then held in darkness for an additional 1–2 hrs.

Individual testing in a darkened room at 22° C. began by allowing the beetle to climb onto or be placed approximately midway up the vertical rod of the "T." In response to a positive phototaxis to light from a flashlight mounted above the "T" and negative geotaxis, the beetles generally climbed upward. Once the insect began waving its antennae, presumably in response to test odors, its forward progress continued. Orientation was scored as soon as the test insect had moved completely from the horizontal to one of the 45° extension arms of the bioassay device. Following each test, the bioassay device was cleaned with acetone to remove contamination left by the insect. For any given series of tests, approximately half were done with the treatment and associated test apparatus on one side, and half were done with them on the other side.

Laboratory bioassays were assessed for significant differences by the hypothesis on binomial proportions based on the standard normal approximation (Brase, C. H., and C. P. Brase (1983), Understanding Statistics, Lexington, Mass.: D. C. Heath).

Results:

Neural Detection of Volatiles Released by Host Plant and CPB Feeding:

Coupled gas chromatography/electroantennogram detection (GC/EAD) with both male and female antennal preparations revealed similar selectivity for both sexes for volatiles released by undamaged plants, mechanically-damaged plants, females or males feeding on the plant (FIG. 1).

Nonanal was the most often detected compound released from an undamaged plant (FIG. 1A). Small quantities of sesquiterpenes and other compounds were released by undamaged plants but seldom were significant antennal responses noted for these compounds.

Figure 3:
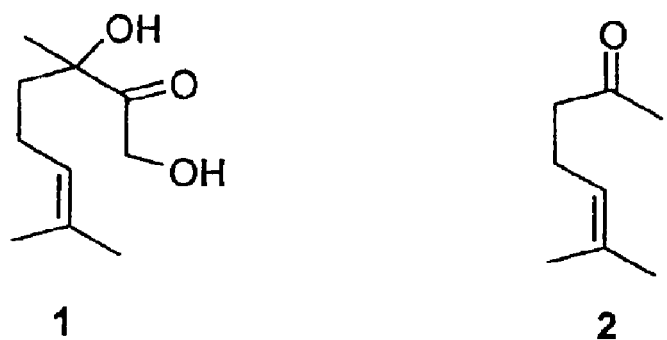
FIG. 3 shows structure of CPB male-specific compound (S)-3,7-dimethyl-2-oxo-oct-6-ene-1,3-diol (1) and related compound 6-methyl-5-heptene-2-one (2).

Relative to undamaged plants, larger amounts of volatiles were emitted by plants that had been mechanically-damaged (FIG. 1B). While EAD responses were present for nonanal as for undamaged plants, an EAD response for 2-phenyl ethanol was also observed. Plants treated in this manner emitted relatively larger amounts of sesquiterpenes. Similar to the mechanically-damaged plants, EADs in response to female feeding were most often to nonanal and 2-phenyl ethanol (FIG. 3C). The quantities of sesquiterpenes emitted by female feeding were less than quantities emitted by mechanically-damaged plants.

EAD responses to volatile collections during male feeding on potato plant differed from responses to undamaged, mechanically-damaged, and female feeding; a large EAD was consistently present in an area just prior to the sesquiterpenes (FIG. 1D). Responses at this retention time were only observed for volatile collections from males; thus this EAD response represented a sex specific, male produced volatile (CPB I). Under these conditions, no observable peak was present from the flame ionization detector. EADs were also observed for nonanal and frequently 2-phenyl ethanol as for volatile collections from undamaged plants, mechanically-damaged plants, and females feeding on plant.

Figure 2:
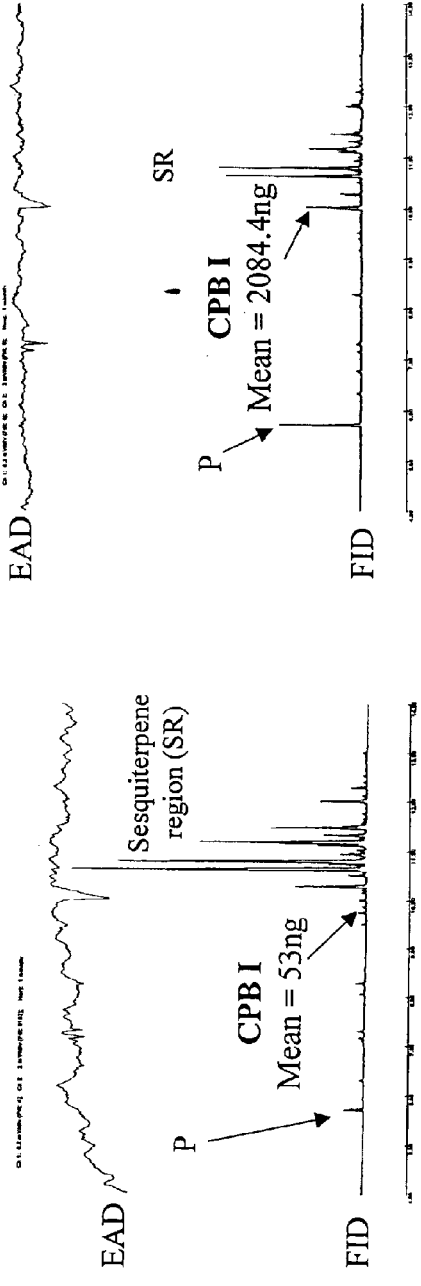
FIG. 2 shows production of male-specific compound (24 hour collection), CPB I, by 20 untreated male CPB (A) and enhancement of CPB I production by experimental treatments (1 μl injection of 50 μl rinse): (B) topical treatment with 10 μg of juvenile hormone III (JH III), (C) antennectomy, and (D) combined treatments topical application of JH III and antennectomy. CPB I=male-specific compound; P=6-methyl-5-hepten-2-one; FID=response of flame ionization detector. Electroantennogram (EAD) response is included for A–C.
Figure 2:
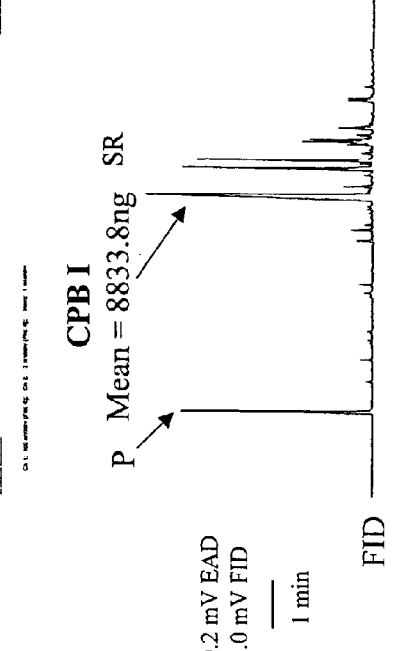
Figure 2:
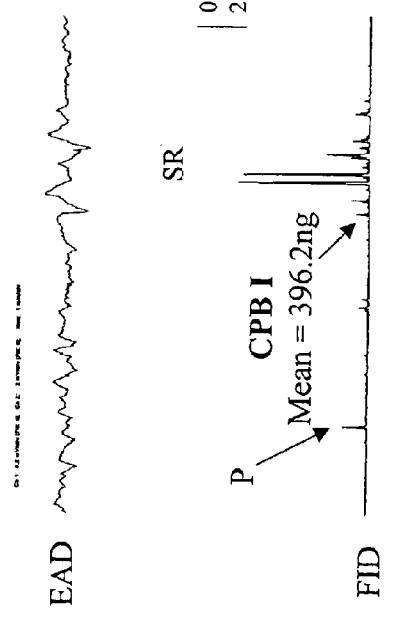

Enhancement of Sex-specific, Male Produced Volatile:

Aerations of ten CPB males feeding on a potato plant in our initial experiments did not yield adequate amounts of the male-specific compound for visualization of a peak on the flame ionization detector. Therefore volatiles were collected from twenty males feeding on potato foliage in a collection chamber with a smaller volume (3 L) (FIG. 2A). Collections done in this manner generally presented a visible peak representing only a few nanograms (mean=53 ng) for the 24 hour collection period, still an inadequate amount for identification.

In order to further enhance production of the male-specific chemical, three techniques were tested for their usefulness (Dickens, J. C., et al., J. Entomol. Sci., 23: 52–58 (1988)): (1) topical treatment with juvenile hormone (JH) III; (2) antennectomy; and (3) tropical treatment with juvenile hormone III and antennectomy. Treatment with JH III enhanced production of the male compound by eightfold to 396.2 ng (FIG. 2B). Antennectomy resulted in a fortyfold increase in production of CPB I (FIG. 2C) relative to untreated males with little effect on quantities of sesquiterpenes collected. The combined treatment of JH III and antennectomy enhanced collections of CPB I by nearly 200× (8833 ng); levels of the male-specific compound that greatly facilitated collection of quantities adequate for identification. Concurrent with the increase in CPB I from antennectomized males and males subjected to the combined treatment was a notable increase in the amount of 6-methyl-5-hepten-2-one, labeled "P" in FIGS. 2C, D.

Identification of Male-specific Compound:

The EAG-active compound was identified as (S)-3,7-dimethyl-2-oxo-oct-6-ene-1,3-diol (1=CPB I)(FIG. 3A). Compound 1 has been reported as a metabolite of geraniol (Devi, J. R., and P. K. Bhattacharyya, Indian J. Biochem. Biophyics, 14: 359–363 (1977)); however, characterization was incomplete, the absolute configuration was not determined, and synthesis was not attempted. A more detailed description of our identification and synthesis will be reported elsewhere, but briefly the initial assignment was made from the compound's electron ionization and chemical ionization mass spectra and an apparent relationship to 6-methyl-5-heptene-2-one (2=P) (FIG. 3B) (a peak for 2 always appeared in gas chromatograms of samples containing 1, and the mass spectra of the two compounds suggested features in common). $^1$H- and $^{13}$C-NMR spectra on material isolated by preparative gas chromatography supported the assignment, and the general structure was finally confirmed by synthesis of racemic 1 from geraniol via its 2,3-monoepoxide. Chiral gas chromatographic comparison to racemic 1 demonstrated that the insect-derived material consisted of a single enantiomer.

Both enantiomers of 1 were then individually synthesized. The terpene linalool was chosen as the starting material because both enantiomers have been fully characterized. (R)(−)-Linalool is commercially available, and the (S)(+)-enantiomer was isolated and purified from oil of coriander (described below). Since the absolute configuration of C-3 of linalool does not change during the synthetic transformations, the configurations of both enantiomers of 1 were thereby established. The absolute configuration of C-3 of insect-derived 1 was found to be (S).

Compound (S)(+)-1 is a clear liquid, $^1$H-NMR 0.91 (s, 3H), 1.14 (s, 3H), 1.42 (s, 3H), 1.40–1.43 (m), 1.72–1.81 (complex multiplet), 2.02 (1H, dd, J=3.0 and 10.0), 2.62 (1H, br. s), 3.61 (1H, d, J=10.4), 3.82 (1H, d, J=10.5). $^{13}$C-NMR 93.63, 83.53, 79.97, 73.72, 48.48, 38.03, 28.03, 24.54, 22.57, 21.54. Mass spectrum (m/z, %) 127 (6), 109 (37), 104 (10), 86 (7), 83 (7), 71 (11), 70 (5), 69 (88), 67 (9), 58 (5), 55 (10), 53 (6), 43 (100), 41 (72). $[\ ]_D^{25}$=+0.73.

Synthesis of (S)(+)-linalool:

Coriander (*Coriandrum sativum* L.) oil has frequently been cited as a source of linalool (A. L. Bandoni, et al., J. Essent. Oil Res., 10: 581–584 (1998); N. Frighetto, et al., J. Essent. Oil Res., 10: 578–580 (1998); G. C. Arganosa, et al., J. Herbs, Spices, and Medicin. Plants, 6(2): 23–32 (1998)) that is generally recognized to be the (S)(+) isomer (in fact, (S)(+)-linalool is occasionally referred to by the trivial name coriandrol; however, the linalool from coriander is not 100% (S), and typically includes 12–15% of the (R)(−)-isomer (Y. Sugawara, et al., Chem. Senses, 25(1): 77–84 (2000); Gaydou, E. M., and R P. Randriamiharisoa, J. Chromatogr., 396: 378–381 (1987)). We investigated a sample of coriander oil that was judged by gas chromatography (GC) to consist of about 67% linalool; the linalool was judged to be about 88% (S) and 12% (R) by GC using a chiral column.

Nonracemic alcohols can sometimes be enantiomerically enriched by recrystallization of their 3,5-dinitrobenzoate esters (Mori, K., and J-L. Brevet, Synthesis, 1125–1129 (1991)). After purification, the alcohols can be easily regenerated by saponification. Described herein is a procedure by which (S)(+)-linalool of essentially 100% chemical purity and >99% enantiomeric purity can be readily obtained from oil of coriander by direct treatment with 3,5-dinitrobenzoyl chloride, purification of the resulting linalool 3,5-dinitrobenzoate, and regeneration of linalool.

Experimental: Gas chromatography (GC) was performed with a Shimadzu Model GC-17A instrument equipped with a 60 m×0.25 mm Rtx™ capillary column and a flame ionization detector, or on a similar instrument equipped with a 30 m×0.25 mm Chiraldex™ B-DM (beta-cyclodextrin dimethyl) column; in the latter case, isothermal operation with hydrogen as carrier at 50 cm/s gave elution times of 15.90 and 16.59 min for the (R) and (S) enantiomers, respectively. Rotations were measured with a Perkin Elmer Model 241 polarimeter. 3,5-Dinitrobenzoyl chloride was purchased from Lancaster Synthesis Inc., Windham, N.H. Pyridine was distilled from calcium hydride prior to use; other solvents were reagent grade and used as received. Oil of coriander was purchased from a local retail store. Linalool was estimated by GC to constitute approximately 67% of the oil, based on a somewhat arbitrary GC evaluation wherein all peaks whose areas represented at least 0.2% of the area of linalool were integrated.

A three-necked flask was fitted with a mechanical stirrer, a thermometer, and an addition funnel protected with a drying tube. 3,5-Dinitrobenzoyl chloride (33.3 g) and 4-(dimethylamino)pyridine (1 g) were introduced, and the solid mixture was stirred while a solution of coriander oil (20 g) in dry pyridine (140 mL) was added at such a rate that the temperature did not exceed 45° C. The solid at first became lumpy but then dispersed as addition continued. After addition the mixture was heated, the solid gradually dissolved and at about 75° C. a dark solution resulted. Stirring was continued at 80–85° C. for an additional hour, then the mixture was cooled and poured into ice water (500 mL). The resulting mixture was extracted with ether (200, then 100 mL); during the process some solid separated that did not readily dissolve. Accordingly, the mixture was then extracted three more times with ethyl acetate (100, then 2×50 mL), and the combined organic extracts were rinsed with water (100 mL), then twice with a mixture of 6N HCl (100 mL) and ice, then again with water (50 mL), with saturated sodium bicarbonate (75 mL), and finally with saturated sodium chloride (75 mL). It was then dried with magnesium sulfate, filtered, and the solvent was stripped on a rotary evaporator to provide 35.7 g of a dark liquid that was flash chromatographed on about 300 g silica gel (although it may be possible to obtain crystalline ester from the crude product, it was our experience that purification proceeded more smoothly if the chromatography step was included.). Elution with petroleum ether (500 mL) followed by 5% EtOAc (1000 mL) and 10% EtOAc in petroleum ether (1400 mL) gave two main fractions, 27.1 g and 4.18 g respectively. The latter fraction, largely unreacted linalool, was distilled to give 2.70 g of pure linalool, b.p. 105° C./30 Torr, $[\alpha]_{25}^D$ (neat)+14.8, enantiomeric composition by GC: 88% (S), 12% (R)).

The major, earlier-eluting fraction slowly began to crystallize upon standing. A few crystals were saved for seed, and the bulk of the material was dissolved in hot 95% ethanol (400 mL) in an Erlenmeyer flask. The flask was then transferred to an ice-water bath and stirred vigorously with a magnetic stirrer (linalool 3,5-dinitrobenzoate tended to separate as an oil if allowed to cool undisturbed). After the temperature had dropped to below room temperature, the solution was seeded to initiate crystallization. A white solid separated, and after a few minutes of stirring the mixture was transferred to a freezer and allowed to cool thoroughly. The solid was collected by suction filtration and rinsed with pre-cooled 95% ethanol. As soon as most of the solvent had been removed, the solid was transferred, with the aid of boiling alcohol, back to the Erlenmeyer flask (the collected material is a heavily solvated, somewhat pasty white solid; when dry, its melting point is about 50° C., but when solvated it can be much nearer room temperature, and the solvated dinitrobenzoate can begin to melt during air-drying if left unattended; if drying is desired, it is recommended to switch the Büchner funnel to a clean suction flask after most of the solvent has been collected) and the crystallization process was repeated four more times with slightly decreasing volumes of solvent, retaining mother liquors for further processing. Upon completion of the fifth crystallization (the progress of enantiomeric enhancement was followed by combining ca. 1 mg of the dinitrobenzoate with a drop or two of methanol and about 20 µL 1N NaOH in a small vial, allowing to stand at room temperature 15–30 min, then further diluting with water and shaking with ca. 0.5–1 mL EtOAc; a portion of the upper layer was transferred by pipette to a clean vial containing a few mg magnesium sulfate, and the dried solution was analyzed by GC with a chiral column (the Chiraldex B-DM column described herein provided satisfactory separation)), the white solid was air dried (7.2 g, 99.2% (S), 0.8% (R)).

The mother liquors accumulated to this point were combined, concentrated to about 200 mL with a rotary evaporator, and chilled in a freezer. A semicrystalline material separated and was recrystallized six times as described above, but with slightly smaller volumes of ethanol, to give 2.7 g additional dinitrobenzoate that was 99.4% (S), 0.6% (R)).

The (S)-linalool dinitrobenzoate thus obtained (9.9 g) had m.p. 49.5–50° C., $[\alpha]^D_{25}$+15.3 (116 mg/mL, CHCl$_3$)(hexane can also be used as a recrystallization solvent for the dinitrobenzoate). Several melting points for linalool 3,5-dinitrobenzoate have appeared in the literature: 135° C. (L. Peyron, Bull. Soc. Chim. Fr., 613–614 (1960)); 87–88° C. (H. Schmidt, et al., Arch. Pharm., 296(8): 544–548 (1963)); 85–87° C. (M. V. Schantz, et al., J. Chromatogr., 38: 364–372 (1968)). In none of these cases was the enantiomeric composition established, and in some cases no recrystallization solvent was specified. The m.p. reported here for the (S)(+)-enantiomer, 49.5–50° C. (open capillary, oil bath), was sharp and reproducible).

The entire sample (9.9 g, 28.5 mmol) was suspended in methanol (75 mL) and stirred under an argon atmosphere while 1 N NaOH (50 mL) was added from an addition funnel. A pink color developed and the white solid gradually dissolved over a 2-hr period. Soon thereafter, another white solid (sodium 3,5-dinitrobenzoate) began to separate. After a total of four hours the mixture was diluted with ice water and extracted with ether-hexanes (1:1, 4×20-mL). The combined organic extracts were rinsed sequentially with water and saturated NaCl, then were dried and concentrated to give 4.59 g of a clear liquid that was distilled to give 3.93 g of (S)(+)-linalool, b.p. 98–100° C./19 Torr, $[\alpha]^D_{25}$ (neat)+18.6 (a value of +18.2 was recently reported (P. J. Landolt, et al., J. Chem. Ecol., 20(11): 2959–2974 (1994)) for a sample of synthetic (S)(+)-linalool whose composition was 97.5% (S) and 2.5% (R)).

Figure 4:
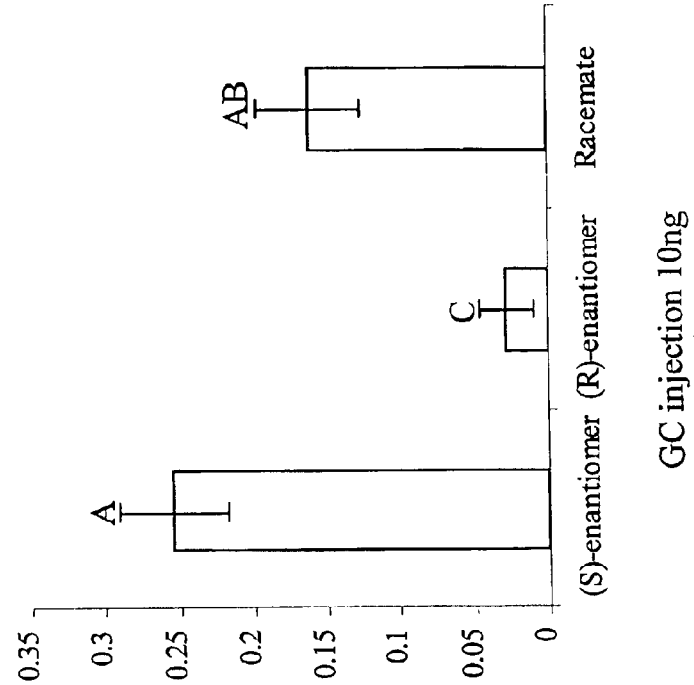
FIG. 4(A) shows single cell recording of receptor neuron response to an airstream contaning volatiles emanating from 100 ng source loads: (2) racemic CPB I, (3) (S)-CPB I, and (4) (R)-CPB I. Control (1) is activity elicited by 5 μl of hexane solvent on filter paper.
FIG. 4(B) shows mean electroantennograms from CPB elicited by 10 ng injection of (S)-enantiomer, (R)-enantiomer, and racemic CPB I. Responses of males and females were not significantly different and thus were combined. Vertical bars represent standard errors (N=6, 3 males and 3 females). Bars with different letters are significantly different, P<0.05, Duncan's multiple range test.
Figure 4:
Figure 4:
Figure 4:
Figure 4:

Antennal Receptors for CPB I Respond Selectively to (S)-enantiomer:

Electrical recording of neuronal activity within a short sensillum on the penultimate antennal segment of a CPB revealed selective responses to optical isomers of CPB I (FIG. 4A). The (S)-enantiomer stimulated 25 action potentials during 500 msec following the initial phasic increase compared to only 9 action potentials for the same time period for the (R)-enantiomer. An intermediate number of action potentials (18) was elicited by the racemic CPB I; only 8 action potentials occurred during the same time period for the solvent control.

Electroantennogram recordings could be correlated with the single cell recording. Mean EAG values were significantly greater for the (S)-enantiomer than the (R)-enantiomer (FIG. 4B). An intermediate response was elicited by an equal amount of the racemate. There were no sexual differences in EAGs to either enantiomer or the racemate at this dose.

Figure 5:
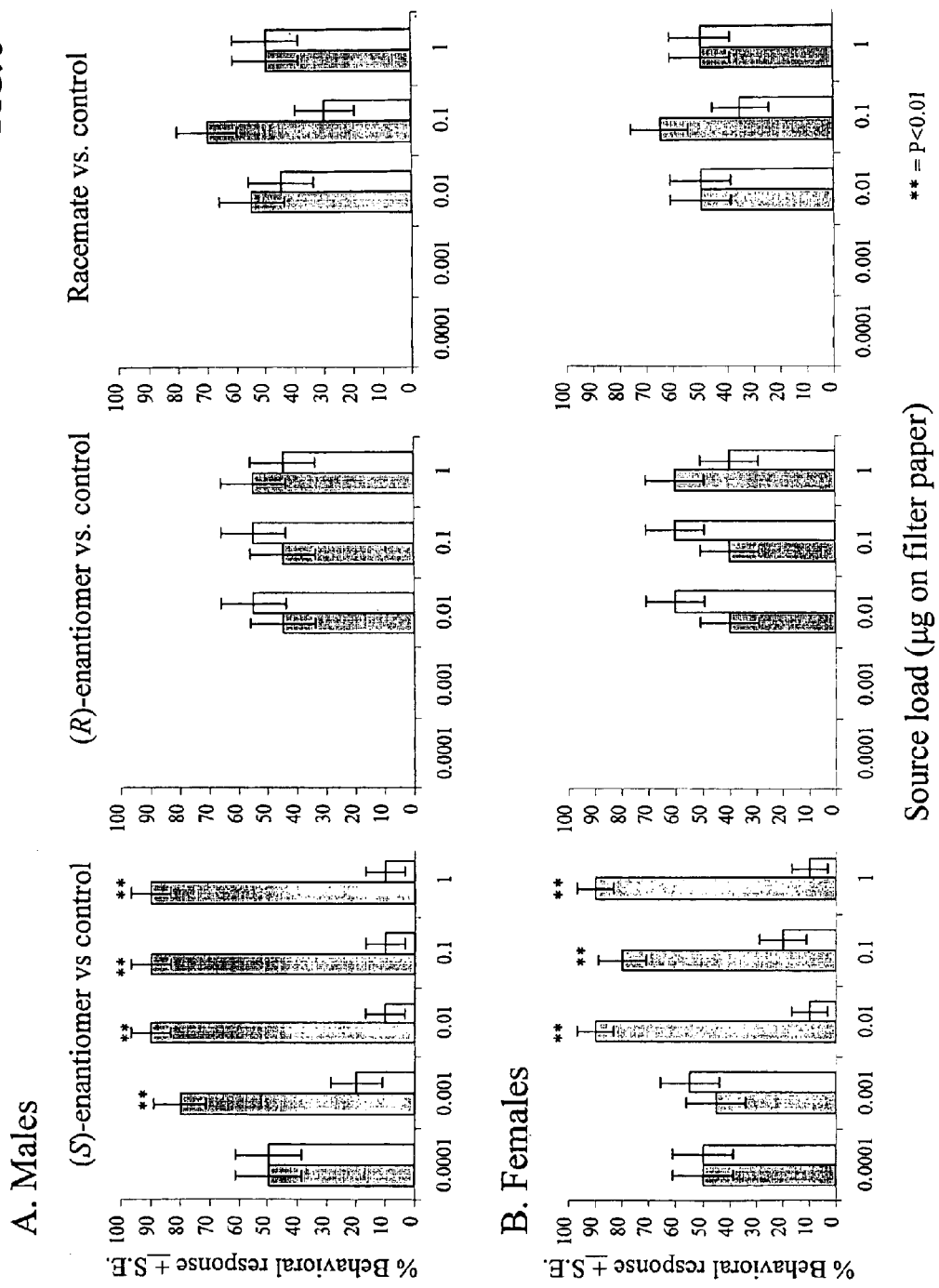
FIG. 5 shows behavioral response of male (A) and female (B) Colorado potato beetles to volatiles emanating from serial source loads of (S)-CPB I=(S)-enantiomer, (R)-CPB I=(R)-enantiomer, and racemic CPB I=Racemate versus solvent control. Shaded bars represent response to experimental treatment; open bars represent response to solvent control. Asterisks indicate that response to experimental treatment differs from control (**=P<0.01) by testing the hypothesis that the binomial proportion is significantly different from P=50% using the standard normal approximation (Brase, C. H., and C. P. Brase, (1983), Understanding Statistics, Lexington, Mass.: D. C. Heath).

Behavioral Activity of Optical Isomers:

Both male and female CPB oriented preferentially to the (S)-enantiomer of CPB I (FIGS. 5A and 5B) (P<0.01). Responses of males had a threshold of only 0.001 µg source load; female CPB had a slightly higher behavioral threshold of 0.01 µg source load. Once reaching threshold for both sexes, 80% to 90% of all individuals were attracted to the (S)-enantiomer through the highest source load tested (1 µg). There was no significant preference for serial source loads of either the (R)-enantiomer or the racemate for either sex.

Discussion:

We have reported herein a volatile attractant pheromone for the Colorado potato beetle that is surprisingly produced only by male beetles. Previous studies on pheromonal communication in the CPB indicated the presence of a volatile female-produced attractant that increased positive anemotaxis in males (DeWilde, J., et al., Netherlands J. Plant Pathol., 75: 53–57 (1969)) or movement of males to a potato plant housing females (Edwards, M. A., and W. D. Seabrook, Canad. Entomol., 129: 667–672 (1997)); (see also Levinson, H. Z., et al., Naturwissenschaften, 66: 472–473 (1979); Jermy, T. and B. A. Butt, Ent. Exp. Appl., 59: 75–78 (1991)). The attraction of CPB to volatiles emanating from potato plants is well-known (McIndoo, N. E., J. Econ. Entomol., 19: 545–571 (1926); Schanz, M.; Z. vergl. Physiol., 35: 353–379 (1953); DeWilde, J., et al., Netherlands J. Plant Pathol., 75: 53–57 (1969); Visser, J. H., Ent. exp. Appl., 20: 275–288 (1976); Bolter, C. J., et al., J. Chem. Ecol., 23: 1003–1023 (1997); Schüitz, S., et al., Naturwissenschaften, 84: 212–217 (1997)) and recently specific blends of volatiles emitted by potato plants that attract CPB have been identified (Dickens, J. C., Agric. Forest Entomol., 2: 167–172 (2000)).

Emission of CPB I by male CPB was at extremely low levels; thus the need to increase production levels for identification. Although JH III clearly increased the amount of CPB I emitted by male CPB, the effect of antennectomy was even more apparent (FIGS. 4B and C). The combination of JH III treatment and antennectomy increased specifically quantities of CPB I released by 166 times the amount released by control insects under similar conditions.

The male produced pheromone for CPB is the first to be identified for a chrysomelid beetle. CPB I has been reported as a metabolite of geraniol, however the structure is unique for an insect pheromone. Previous pheromones identified for chrysomelids have been female-produced sex attractants (Mayer, M. S., and J. R. McLaughlin, 1991, Handbook of Insect Pheromones and Sex Attractants. Boca Raton, Fla., CRC Press, 1083 pp.). Recently, field trapping experiments indicated that male crucifer flea beetles, *Phyllotreta cruciferae* (Goeze), may produce an aggregation pheromone but the nature of the attractant was not elucidated (Peng, C., et al., Physiol. Entomol., 24: 98–99 (1999)).

In conclusion, we have identified a male-produced aggregation pheromone, (S)-CPB I, for the CPB. Production of (S)-CPB I was enhanced by topical application of JH III and antennectomy, and, thus, levels may be regulated by antennal input and under hormonal control. Only (S)-CPB I is released by males; (S)-CPB I is attractive in laboratory behavioral bioassays for both male and female CPB, while (R)-CPB I was inactive and its presence in the racemate diminishes response to the (S)-enantiomer. The male-produced aggregation pheromone will provide an additional tool for use in conjunction with previously identified plant attractants (Dickens, J. C., Agric. Forest Entomol., 1: 47–54 (1999); Dickens, J. C., Agric. Forest Entomol., 2: 167–172 (2000)) already being tested in the field (Martel, J. W., A. R. Alford, and J. C. Dickens, "Alternative management of Colorado potato beetle, *Leptinotarsa decemlineata* (Say), using a host plant volatile-based attractant," Z. angew. Entomol., Submitted (2001)) for manipulation of chemically mediated behavior for environmentally sound pest management.

Laboratory Behavioral Bioassays:

Insects: All life stages were reared on potted potato plants kept in screened cages inside incubators set for 16L:8D, 25° C. during photophase, 23° C. during scotophase, and 80% R.H. Upon emergence adult beetles were kept individually in plastic cups with perforated plastic snap-on lids, and provided with clean pieces of paper toweling and potato foliage daily.

Bioassay apparatus and protocol: Stock solutions of test compounds, e.g. (S)-CPB I, and individual plant volatiles 2-phenylethanol, nonanal and (±)-linalool, were prepared at 10 $\mu g/\mu l$ in hexane. Serial dilutions were made to obtain a test solution of 0.1 $\mu g/\mu l$. Each bioassay treatment of CPB I used a 10 $\mu l$ aliquot of test solution, or a total of 1 $\mu g$ of neat material. A 500 $\mu g/\mu l$ stock solution of a 3-component blend of selected potato volatiles, (Z)-3-hexenyl acetate, linalool, and methyl salicylate, was prepared as follows: 8.3 $\mu l$ of each was added to 975 $\mu l$ of mineral oil, creating a solution of 25 $\mu g$ of blend components/$\mu l$. This stock solution was diluted to obtain a solution of 2.5 $\mu g$ of blend components/$\mu l$. Each bioassay treatment of blend used a 20 $\mu l$ aliquot of test solution, or a total of 50 $\mu g$ (16.67 $\mu g$/component) of the components.

Prior to testing at age 7–14 days, unmated insects were held individually in 5.5 oz. cups, provided with fresh potato foliage on a continuous basis, and maintained under incubator conditions of 16L:8D, 80–90% R.H., and "day" and "night" temperatures of 25° C. and 23° C., respectively. On the day of testing, insects were transferred to smaller 1 oz. cups and held for 1–3 hrs with moist filter paper but no foliage, then held in darkness for an additional 1–2 hrs.

Individual chemicals and chemical blends were tested for activity in an open Y-track olfactometer modified after Visser and Piron (1998) and described in detail by Dickens (1999; 2000; and Dickens, J. C., et al., Breaking a paradigm: male-produced aggregation pheromone for Colorado potato beetle. *Journal of Experimental Biology*, 205: 1925–1933 (2002)). In brief, odorous stimuli emanating from synthetic blends on filter paper discs (2.5 cm dia.; Whatman™ #1 filter paper) in 500 ml Ehrlenmeyer flasks were delivered to either side of the device. Test odorants were pipetted onto 3-cm diam. filter paper disks, which were then transferred, using long forceps, into the Erlenmeyer flasks used in the assay. If only a single test solution were being used per treatment, it was placed in the center of the filter paper; if 2 test solutions were being used per treatment, the mineral oil solution was placed in the center, and the hexane solution was spotted around the edge of the filter paper disk. Treatments were replaced after 30 minutes of testing in order to minimize variation in odor concentrations. The location of the chemical blend was switched from one side of the bioassay apparatus to the other side midway through each run in order to avoid bias not associated with the experimental treatment. Chemicals tested, their source and purity are given in Table 1. Hydrocarbon free air that was humidified by passing through distilled water carried the odor molecules to either arm of the bioassay apparatus. Airflow was regulated to 1 l/min by flow meters. Experiments were conducted in a darkened room at 22° C. in which the only source of light was that associated with the bioassay device. For all bioassays at least 40 adults (20 males and 20 females) were tested. Orientation was scored as soon as the test insect had moved completely from the horizontal to one of the 45° angle extension arms of the bioassay device. Following each test, the bioassay device was cleaned with acetone to remove contamination left by the insect.

Statistical analysis: Laboratory bioassays were assessed for significant differences by the hypothesis on binomial proportions based on the standard normal approximation (Brase and Brase, 1983).

Field Tests:

Insects: Insects were maintained under the same regimen as for laboratory bioassays. Prior to release in the field, adult CPB were combined into pint containers with moistened paper and potato foliage in groups of 25. Insects were removed from foliage ca. 3 hours prior to release.

Chemical treatments: (S)-CPB I vs. control. CPB I was dissolved into a carrier solution of 20% polyethylene glycol, 42% methanol, 25% glycerol, and 13% distilled water at a concentration of 1 $\mu g/\mu l$. For treatment lures, 500 $\mu l$ were injected into 1" long cigarette filters (500 $\mu g$ CPBI/lure). Control lures consisted of 1" cigarette filters treated with 500 $\mu l$ of the carrier solution. Lures were prepared and placed into plastic zip-lock bags for transport to the field. (S)-CPB I+3-component plant blend vs. 3-component plant blend. (Z)-3-hexenyl acetate, (±)-linalool, and methyl salicylate (10 $\mu l$ each) were added to 3 ml of the carrier solution for a total concentration of 1%. This solution was split into two 1.5 ml samples and CPB I dissolved into one of the samples at a concentration of 1 $\mu g/\mu l$. One treatment consisted of 500 $\mu l$ of 1% 3-component plant blend injected into 1" cigarette filters, 500 $\mu l$ of 1% 3-component plant blend+1 $\mu g/\mu l$ CPB I (500 $\mu g$ CPB I/lure) injected into 1" cigarette filters comprised the second treatment. Lures were prepared and placed into zip-lock bags for transport to the field.

Experimental procedure: Six pitfall traps (22 cm diam.× 21 cm depth) were set in a hexagonal pattern 6 m diameter in an isolated grass field mowed one day prior to release of insects. One lure was attached to a 1 m vertical yellow posts set through the center of each pitfall trap, with treatment and controls alternating around the hexagonal array. Tacky-trap was laced along the rim of each pitfall trap, and on the center post at trap level, to prevent insect escape. One hundred male or female CPB were released in the center of the trap array between 1200 (Noon)-1400 (2 pm) hr. Insects were removed from the traps at 3-hour intervals following release between 0800 (8 am) through 2000 (8 pm) hr. Captured insects were sexed to confirm gender.

Statistical analysis: Field tests were assessed for significant differences by a paired t-test (Ostle, B., Statistics in Research (1963), $2^{nd}$ ed., The Iowa State University Press, Ames, Iowa).

Results:

Laboratory Behavioral Bioassays:

(S)-CPB I attracted both male and female beetles at the dose tested (P<0.05) as previously shown (Dickens et al. 2002)(Table 2, first treatment pair). When offered a choice between (S)-CPB I and a previously identified three-component plant attractant blend no preference was shown for either attractant (Table 2, second first treatment pair). The combination of the pheromone (S)-CPB I and plant blend was attractive to male beetles while females showed no preference (Table 2, third first treatment pair). Both male and female beetles preferred the combination of the pheromone and plant attractant to either the plant blend or pheromone alone (Table 2, fourth and fifth first treatment pairs).

Combinations of the pheromone with volatiles released by potato plants and detected by CPB antennal receptors produced interesting results. (S)-CPB I combined with 2-phenylethanol attracted male CPB while females showed no preference for the combination versus the solvent control (Table 2, sixth first treatment pair). However addition of either nonanal or linalool to the aforementioned two component blend formed three component blends that attracted both sexes (Table 2, seventh and eighth first treatment pairs).

Field Tests:

Significantly more male and female CPB were captured in pitfall traps baited with the aggregation pheromone (S)-CPB I than control traps (Table 3, P<0.05). The combination of the pheromone with the plant attractant blend captured more males and females than the plant attractant alone (Table 3, P<0.05).

In summary, a male-produced aggregation pheromone was identified for the Colorado potato beetle (CPB) *Leptinotarsa decemlineata* (Say) (*Coleoptera:Chrysomelidae*). While male beetles produced only minor amounts of the pheromone, its production could be enhanced by topical application of juvenile hormone III, antennectomy, or the combined treatment of JH III and antennectomy; this enhancement facilitated the identification of the compound as (S)-3,7-dimethyl-2-oxo-oct-6-ene-1,3-diol [=(S)-CPB I], a unique structure for an insect pheromone. Antennal receptors responded selectively to the (S)-enantiomer. Both male and female CPB were attracted to serial source loads of (S)-CPB I in laboratory bioassays; (R)-CPB I was inactive or inhibitory as evidenced by the inactivity of the racemate. This is the first identification of a pheromone for the CPB and differs from the paradigm of a female-produced pheromone for this insect. The male-produced attractant is also the first identified for the Chrysomelidae.

All of the references cited herein are incorporated by reference in their entirety. U.S. patent application Ser. No. 09/925,131, filed on Aug. 9, 2001, and U.S. Provisional Patent Application No. 60/225,789, filed on Aug. 17, 2000, are incorporated herein by reference in their entirety. Also incorporated herein by reference in their entirety are the following: Borden, J. H., et al., Science, 166: 1626 (1969); Hughes, P. R,. and J. A. A. Renwick, Physiol. Entomol., 2: 117–123, 289–292 (1977); Renwick, J. A. A,. and J. C. Dickens, Physiol. Entomol., 4: 377–381 (1979); Dickens, J. C., et al.,. J. Entomol. Sci., 23: 52–58 (1988); Palaniswamy, P. P., et al., J. Insect Physiol,. 25: 571–574 (1979); Dickens, J. C., 1986, Specificity in perception of pheromones and host odours in Coleoptera, In *Mechanisms in Insect Olfaction* (eds. T. L. Payne, M. C. Birch and C. Kennedy), pp. 253–261, Oxford, U. K., Oxford University Press).

Thus, in view of the above, the present invention concerns (in part) the following:

(S)-3,7-dimethyl-2-oxo-oct-6-ene-1,3-diol.

A composition (with or without an insecticide) for attracting Colorado potato beetles (male, female, or both male and female), comprising (or consisting essentially of or consisting of) a carrier material and a Colorado potato beetle attracting effective amount of (S)-3,7-dimethyl-2-oxo-oct-6-ene-1,3-diol.

The above composition further containing an insecticide.

The above composition further containing (a) (Z)-3-hexenyl acetate, (±)-linalool, nonanal, and methyl salicylate; (b) (Z)-3-hexenyl acetate, (±)-linalool, and methyl salicylate; (c) (Z)-3-hexen-1-ol, (E)-2-hexen-1-ol, and (±)-linalool; (d) (Z)-3-hexenyl acetate and methyl salicylate; (e) (Z)-3-hexenyl acetate and (±)-linalool; (f) (Z)-3-hexen-1-ol, (E)-2-hexen-1-ol, (±)-linalool, nonanal, and methyl salicylate; (g) nonanal; (h) 2-phenylethanol; (i) 2-phenylethanol and (±)-linalool; or (j) 2-phenylethanol and nonanal.

The above composition further containing(Z)-3-hexenyl acetate, (±)-linalool, and methyl salicylate.

The above composition further containing at least one member selected from the group consisting of (Z)-3-hexenyl acetate, (±)-linalool, nonanal, methyl salicylate, (Z)-3-hexen-1-ol, (E)-2-hexen-1-ol, nonanal, 2-phenylethanol, and mixtures thereof.

The above composition, wherein the composition contains from about 0.00001% to about 99.99% of said (S)-3,7-dimethyl-2-oxo-oct-6-ene-1,3-diol (or from about 0.00001% to about 50%, or from about 0.00001% to about 10%, or from about 0.00001% to about 1%, or from about 0.00001% to about 0.1%, or from about 0.00001% to about 0.01% of (S)-3,7-dimethyl-2-oxo-oct-6-ene-1,3-diol).

A method for attracting Colorado potato beetles (male or female or both male and female) to an object or area, comprising (or consisting essentially of or consisting of) treating the object or area with a Colorado potato beetle attracting composition (with or without an insecticide) comprising (or consisting essentially of or consisting of) a carrier material and a Colorado potato beetle attracting effective amount of (S)-3,7-dimethyl-2-oxo-oct-6-ene-1,3-diol.

The above method, wherein said composition further contains at least one member selected from the group consisting of (Z)-3-hexenyl acetate, (±)-linalool, nonanal, methyl salicylate, (Z)-3-hexen-1-ol, (E)-2-hexen-1-ol, nonanal, 2-phenylethanol, and mixtures thereof.

The above method, wherein said composition further contains (Z)-3-hexenyl acetate, (±)-linalool, and methyl salicylate.

The above method, wherein the composition contains from about 0.00001% to about 99.99% of said (S)-3,7-dimethyl-2-oxo-oct-6-ene-1,3-diol (or from about 0.00001% to about 50%, or from about 0.00001% to about 10%, or from about 0.00001% to about 1%, or from about 0.00001% to about 0.1%, or from about 0.00001% to about 0.01% of (S)-3,7-dimethyl-2-oxo-oct-6-ene-1,3-diol).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Source and purity of chemicals used in behavioral tests, and their presence in volatile emissions of intact (IP), damaged (DP) or male CPB feeding (ME) on potato plants (Bolter et al., 1997; Schultz et al., 1997; Dickens et al., 2002).

| Chemical | Source[1] | Purity (%) | Presence in intact plant (IP), damaged plant (DP), or presence in emissions of males feeding on plant (ME) |
|---|---|---|---|
| Pheromone | | | |
| (S)-CPB I | A | >99 | ME III |
| Green leaf volatile | | | |
| (Z)-3-hexenyl acetate | C | 98 | DP I |
| Aliphatic aldehyde | | | |
| nonanal | B | 95 | IP I, II; DP I, II; ME III |

TABLE 1-continued

Source and purity of chemicals used in behavioral tests, and their presence in volatile emissions of intact (IP), damaged (DP) or male CPB feeding (ME) on potato plants (Bolter et al., 1997; Schültz et al., 1997; Dickens et al., 2002).

| Chemical | Source[1] | Purity (%) | Presence in intact plant (IP), damaged plant (DP), or presence in emissions of males feeding on plant (ME) |
|---|---|---|---|
| Oxygenated monoterpene | | | |
| (±)-linalool | B | 97 | IP I; DP I, II |
| Benzene derivative | | | |
| methyl salicylate | B | 99 | DP I |
| 2-phenylethanol | C | >99 | DP II, III; ME III |

[1]A-Synthesized by Dr. J. E. Oliver; B-Aldrich Chemical Co., P.O. Box 14508, St. Louis, MO 63178 USA; C-Sigma Chemical Co., P.O. Box 14508, St. Louis, MO 63178 USA.
[2]I-Bolter et al., 1997; II-Schültz et al., 1997; III-Dickens et al., 2002.

TABLE 2

Orientation of male and female Colorado potato beetles to pheromone, (S)-CPB I vs the three component Plant Blend (Z)-3-hexenyl acetate + (±)-linalool + methyl salicylate (Dickens, 2000). Control = Equal amount of solvent (i.e. 10 μl hexane for (S)-CPB I and other individual compounds, and 20 μl mineral oil for Plant blend). Asterisks indicate that response to experimental treatment differs from control (* = P < 0.05, ** = P < 0.01) by testing the hypothesis that the binomial proportion is significantly different from P = 50% using the standard normal approximation (Brase and Brase, 1983). See text for details.

| | Treatment pair A. vs. B. | Male #A. vs. #B. % to A. | Female #A. vs. #B. % to A. | Total #A. vs. #B. % to A. |
|---|---|---|---|---|
| I | A. (S)-CPB I vs. B. Control | 18 vs. 2 90%** | 18 vs. 2 90%** | 36 vs. 4 90%** |
| II | A. (S)-CPB I vs. B. Plant blend | 10 vs. 10 50% | 10 vs. 10 50% | 20 vs. 20 50% |
| III | A. (S)-CPB + Plant blend vs. B. Control | 19 vs. 1 95%** | 11 vs. 9 55% | 30 vs. 10 75%** |
| IV | A. (S)-CPB I + Plant blend B. Plant blend | 18 vs. 2 90%** | 19 vs. 1 95%** | 37 vs. 3 92.5%** |
| V | A. (S)-CPB I + Plant blend B. (S)-CPB I | 15 vs. 5 75%* | 17 vs. 3 85%** | 32 vs. 8 80%** |
| VI | A. (S)-CPB I + 2-phenylethanol B. Control | 57 vs. 13 81.4%** | 33 vs. 37 47.1% | 90 vs. 50 64.3% |
| VII | A. (S)-CPB I + 2-phenylethanol + nonanal B. Control | 19 vs. 1 95%** | 16 vs. 4 80%** | 35 vs. 5 87.5%** |
| VIII | A. (S)-CPB I + 2-phenylethanol + linalool B. Control | 15 vs. 5 75%* | 15 vs. 5 75%* | 30 vs. 10 75%** |

TABLE 3

Mean number of Colorado potato beetles captured in pit-fall traps in the field baited with (S)-CPB I vs. Control. Males = mean of three replicates; females = mean of three replicates. Total = combined mean of six replicates (three male + three female). Asterisks indicate that response to experimental treatment differs from control (* = P < 0.05, ** = P < 0.01) by a paired t-test (Ostle, 1963). See materials and methods for details.

| | Number of CPB captured | | |
|---|---|---|---|
| Treatment | Males | Females | Total |
| (S)-CPB I | 9.00* (27) | 7.33* (22) | 8.17** (49) |
| Control | 2.67 (8) | 1.33 (4) | 2.00 (12) |

* = P < 0.05;
** = P < 0.01 paired t-test

We claim:

1. A method for attracting Colorado potato beetles to an object or area, comprising treating said object or area with a Colorado potato beetle attracting composition comprising a carrier material and a Colorado potato beetle attracting effective amount of (S)-3,7-dimethyl-2-oxo-oct-6-ene-1,3-diol.

2. The method according to claim 1, wherein said composition further contains (Z)-3-hexenyl acetate, (±)-linalool, and methyl salicylate.

3. The method according to claim 1, wherein said compostion contains from about 0.00001% to about 99.99% of said (S)-3,7-dimethyl-2-oxo-oct-6-ene-1,3-diol.

4. The method according to claim 1, wherein said composition contains from about 0.00001% to about 50% of said (S)-3,7-dimethyl-2-oxo-oct-6-ene-1,3-diol.

5. The method according to claim 1, wherein said composition contains from about 0.00001% to about 10% of said (S)-3,7-dimethyl-2-oxo-oct-6-ene-1,3-diol.

6. The method according to claim 1, wherein said composition contains from about 0.00001% to about 1% of said (S)-3,7-dimethyl-2-oxo-oct-6-ene-1,3-diol.

7. The method according to claim 1, wherein said composition contains from about 0.00001% to about 0.1% of said (S)-3,7-dimethyl-2-oxo-oct-6-ene-1,3-diol.

8. The method according to claim 1, wherein said composition contains from about 0.0001% to about 0.01% of said (S)-3,7-dimethyl-2-oxo-oct-6-ene-1,3-diol.

9. The method according to claim 1, wherein said composition further contains at least one member selected from the group consisting of (Z)-3hexenyl acetate, (±)-linalool, nonanal, methyl salicylate, (Z)-3-hexen-1-ol, (E)-2-hexen-1-ol, 2-phenylethanol, and mixtures thereof.

10. A composition for attracting Colorado potato beetles, consisting of a carrier material and a Colorado potato beetle attracting effective amount of (S)-3,7-dimethyl-2-oxo-oct-6-ene-1,3-diol, optionally an insecticide, and optionally at least one member selected from the group consisting of (Z)-3-hexenyl acetate, (±)-linalool, nonanal, methyl salicylate, (Z)-3-hexen-1-ol, (E)-2-hexen-1-ol, nonanal, 2-phenylethanol, and mixtures thereof.

11. The composition according to claim 10, wherein said composition contains from about 0.00001% to about 99.99% of said (S)-3,7-dimethyl-2-oxo-oct-6-ene-1,3-diol.

12. The composition according to claim 10, wherein said composition contains from about 0.00001% to about 50% of said (S)-3,7-dimethyl-2-oxo-oct-6-ene-1,3-diol.

13. The composition according to claim 10, wherein said composition contains from about 0.00001% to about 10% of said (S)-3,7-dimethyl-2-oxo-oct-6-ene-1,3-diol.

14. The composition according to claim 10, wherein said composition contains from about 0.00001% to about 1% of said (S)-3,7-dimethyl-2-oxo-oct-6-ene-1,3-diol.

15. The composition according to claim 10, wherein said composition contains from about 0.00001% to about 0.1% of said (S)-3,7-dimethyl-2-oxo-oct-6-ene-1,3-diol.

16. The composition according to claim 10, wherein said composition contains from about 0.0001% to about 0.01% of said (S)-3,7-dimethyl-2-oxo-oct-6-ene-1,3-diol.

17. The composition according to claim 10, wherein said composition contains an insecticide.

18. The composition according to claim 10, wherein said composition contains at least one member selected from the group consisting of (Z)-3hexenyl acetate, (±)-linalool, nonanal, methyl salicylate, (Z)-3-hexen-1-ol, (E)-2-hexen-1-ol, nonanal, 2-phenylethanol, and mixtures thereof.

19. The composition according to claim 10, wherein said composition contains (Z)-3-hexenyl acetate, (±)-linalool, and methyl salicylate.

* * * * *